United States Patent
Diulgheroff et al.

(10) Patent No.: US 7,994,180 B2
(45) Date of Patent: Aug. 9, 2011

(54) PROCESSES FOR PREPARING INTERMEDIATES OF PEMETREXED

(75) Inventors: Nicola Diulgheroff, Turin (IT); Moran Pirkes, Turin (IT); Alessandro Pontiroli, S. Maria della Versa (IT); Marco Villa, Milan (IT)

(73) Assignee: Sicor Inc., Irvine, CA (US)

( * ) Notice: Subject to any disclaimer, the term of this patent is extended or adjusted under 35 U.S.C. 154(b) by 897 days.

(21) Appl. No.: 11/893,233

(22) Filed: Aug. 14, 2007

(65) Prior Publication Data
US 2008/0146799 A1 Jun. 19, 2008

Related U.S. Application Data

(60) Provisional application No. 60/837,303, filed on Aug. 14, 2006, provisional application No. 60/860,557, filed on Nov. 21, 2006, provisional application No. 60/837,637, filed on Aug. 15, 2006, provisional application No. 60/860,554, filed on Nov. 21, 2006, provisional application No. 60/880,178, filed on Jan. 11, 2007, provisional application No. 60/958,213, filed on Jul. 3, 2007, provisional application No. 60/839,551, filed on Aug. 22, 2006, provisional application No. 60/845,031, filed on Sep. 14, 2006, provisional application No. 60/899,928, filed on Feb. 6, 2007, provisional application No. 60/936,553, filed on Jun. 20, 2007, provisional application No. 60/958,413, filed on Jul. 5, 2007, provisional application No. 60/847,291, filed on Sep. 25, 2006, provisional application No. 60/855,139, filed on Oct. 30, 2006, provisional application No. 60/880,179, filed on Jan. 11, 2007, provisional application No. 60/958,326, filed on Jul. 2, 2007.

(51) Int. Cl.
*C07D 487/04* (2006.01)
*A61K 31/519* (2006.01)
*A61P 35/04* (2006.01)

(52) U.S. Cl. .................................. 514/265.1; 544/280
(58) Field of Classification Search .................. 544/280; 514/265.1
See application file for complete search history.

(56) References Cited

U.S. PATENT DOCUMENTS

| 5,344,932 A | 9/1994 | Taylor |
| 5,416,211 A | 5/1995 | Barnett et al. |
| 6,262,262 B1 | 7/2001 | Kjell |
| 7,138,521 B2 | 11/2006 | Chelius et al. |
| 2003/0216416 A1 | 11/2003 | Chelius et al. |

FOREIGN PATENT DOCUMENTS

| EP | 0 432 677 A1 | 6/1991 |
| EP | 0 434 426 A1 | 6/1991 |
| WO | WO 98 08382 | * 3/1998 |
| WO | WO-01/14379 A2 | 3/2001 |
| WO | WO 2008/124485 A2 | 10/2008 |

OTHER PUBLICATIONS

Physicians' Desk Reference, 1722-1728 (60th ed. 2006).
Barnett, Charles, et al., "A Practical Synthesis of Multitargeted Antifolate LY231514," *Organic Process Research & Development*, 3(3): 184-188 (1999).
U.S. Pharmacopeia, 387-389 (30th ed. 2007).
Kjell, Douglas P., et al., "Determination of the Source of the N-Methyl Impurity in the Synthesis of Pemetrexed Disodium Heptahydrate," *Organic Process Research and Development*, 9(6): 738-742 (2005).
International Conference on Harmonisation of Technical Requirements for Registration of Pharmaceuticals for Human Use, ICH Harmoniszed Tripartite Guideline: Good Manufacturing Practice Guide for Active Pharmaceutical Ingredients Q7 (Current Step 4 version, Nov. 10, 2000) (available at http://www.ich.org/LOB/media/MEDIA433.pdf, last visited Dec. 21, 2007).

* cited by examiner

*Primary Examiner* — Susanna Moore
(74) *Attorney, Agent, or Firm* — Merchant & Gould PC

(57) ABSTRACT

The invention provides intermediates of pemetrexed of formula VI and processes for the preparation thereof.

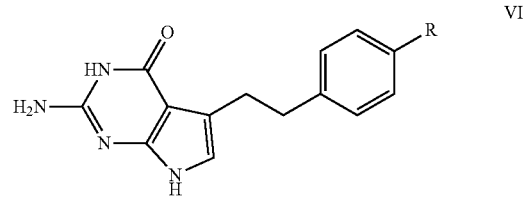

17 Claims, No Drawings

PROCESSES FOR PREPARING INTERMEDIATES OF PEMETREXED

CROSS-REFERENCE TO RELATED APPLICATIONS

This application claims the benefit of U.S. provisional application Ser. Nos. 60/837,303, filed Aug. 14, 2006; 60/860,557, filed Nov. 21, 2006; 60/837,637, filed Aug. 15, 2006; 60/860,554, filed Nov. 21, 2006; 60/880,178, filed Jan. 11, 2007; 60/958,213, filed Jul. 3, 2007; 60/839,551, filed Aug. 22, 2006; 60/845,031, filed Sep. 14, 2006; 60/899,928, filed Feb. 6, 2007; 60/936,553, filed Jun. 20, 2007; 60/958,413, filed Jul. 5, 2007; 60/847,291, filed Sep. 25, 2006; 60/855,139, filed Oct. 30, 2006; 60/880,179, filed Jan. 11, 2007; and 60/958,326, filed Jul. 2, 2007, hereby incorporated by reference.

FIELD OF THE INVENTION

The invention encompasses processes for preparing intermediates of pemetrexed.

BACKGROUND OF THE INVENTION

Compounds known to have antifolate activity are well recognized as chemotherapeutic agents for the treatment of cancer. In particular, compounds in the folic acid family have various activities at the enzymatic level as they inhibit such enzymes as dehydrofolate reductase, folate polyglutamate synthetase, glycinamide ribonucleotide formyltransferase and thymidylate synthetase.

Recently a series of 4-hydroxypyrrolo[2,3-d]pyrimidine-L-glutamic acid derivatives have been disclosed, for example in European publication No. 0434426, and shown to be particularly useful antifolate drugs. Among these 4-hydroxypyrrolo[2,3-d]pyrimidine-L-glutamic acid derivatives is pemetrexed disodium heptahydrate of formula I.

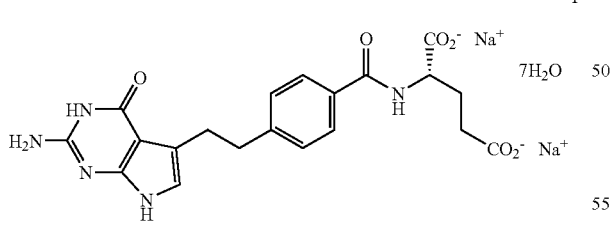

Pemetrexed disodium heptahydrate is a multitargeted antifolate drug approved for treatment of mesothelioma and for second-line treatment of non small cell lung cancer.

Pemetrexed disodium salt heptahydrate is marketed by Eli Lilly and Company under the trade name ALIMTA® as a sterile lyophilized powder for intravenous administration. This member of the folic acid family has been approved for treatment of malignant pleural mesothelioma and for second-line treatment of non small cell lung cancer. See *Physicians' Desk Reference*, 60th ed., pp. 1722-1728 (2006). The commercial product is reported to be a lyophilized powder of heptahydrate pemetrexed disodium and mannitol.

European publication No. 0432677 reports one of the first syntheses of pemetrexed disodium heptahydrate. This route of synthesis, however, is not very suitable for industrial production due to the number of steps and the poor overall yield.

More recent syntheses of pemetrexed disodium heptahydrate (e.g. U.S. Pat. No. 5,416,211) follow a different route through 4-[2-(2-amino-4,7-dihydro-4-oxo-1H-pyrrolo[2,3-d]pyrimidin-5-yl)ethyl]benzoic acid of formula II.

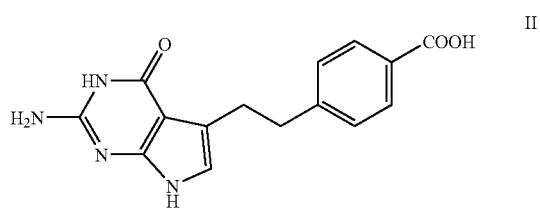

The compound of formula II may be prepared via an intermediate of formula III,

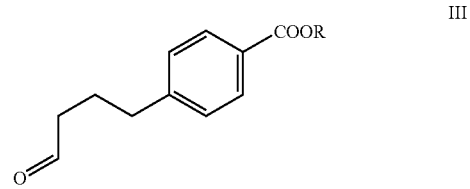

where R is hydrogen or a carboxy protecting group.

U.S. Pat. No. 5,416,211 ("'211 patent") and U.S. Pat. No. 6,262,262 ("'262 patent") disclose the preparation of the compound of formula II by halogenation of the intermediate of formula III to provide the following halo intermediate,

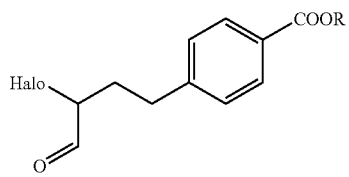

which is not isolated. The halo intermediate is then condensed in-situ with a pyrimidine moiety to form an ester of the following formula IV.

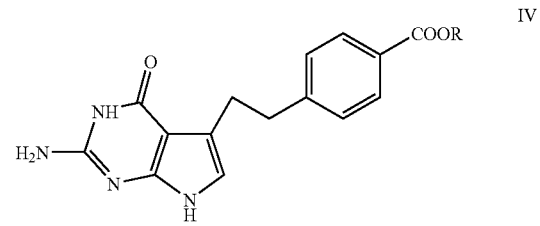

The ester of formula IV is then hydrolyzed to form the compound of formula II. The process is shown in the following scheme I.

Scheme I.

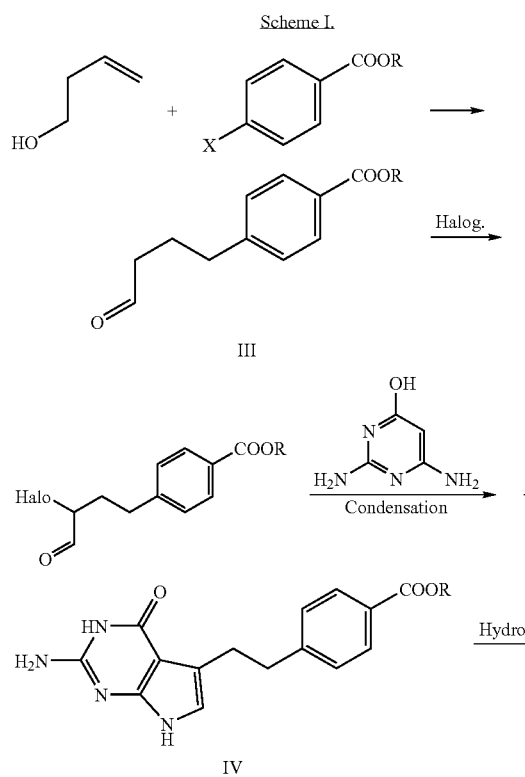

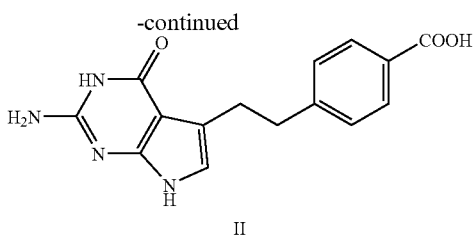

However, the '262 patent reports that the aldehyde intermediate of formula III is obtained with unspecified byproducts, is scarcely stable and tends to decompose during purification. Thus, the '262 patent discloses an additional process wherein the intermediate of formula III is prepared and then transformed into a sulfonic acid metal cation salt of formula V,

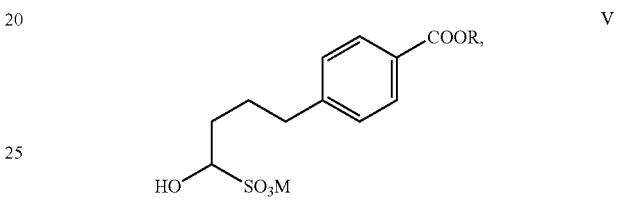

which can be isolated and purified. The intermediate of formula III is then re-generated from sulfonic acid metal cation salt of formula V, transformed in situ into the corresponding alpha-halo derivative and treated with 2,4-diamino-6-hydroxy pyrimidine without isolation of the intermediate to obtain the ester of formula IV. The preparation of compound of formula II via the sulfonic acid metal cation salt of formula V is illustrated by the following scheme II.

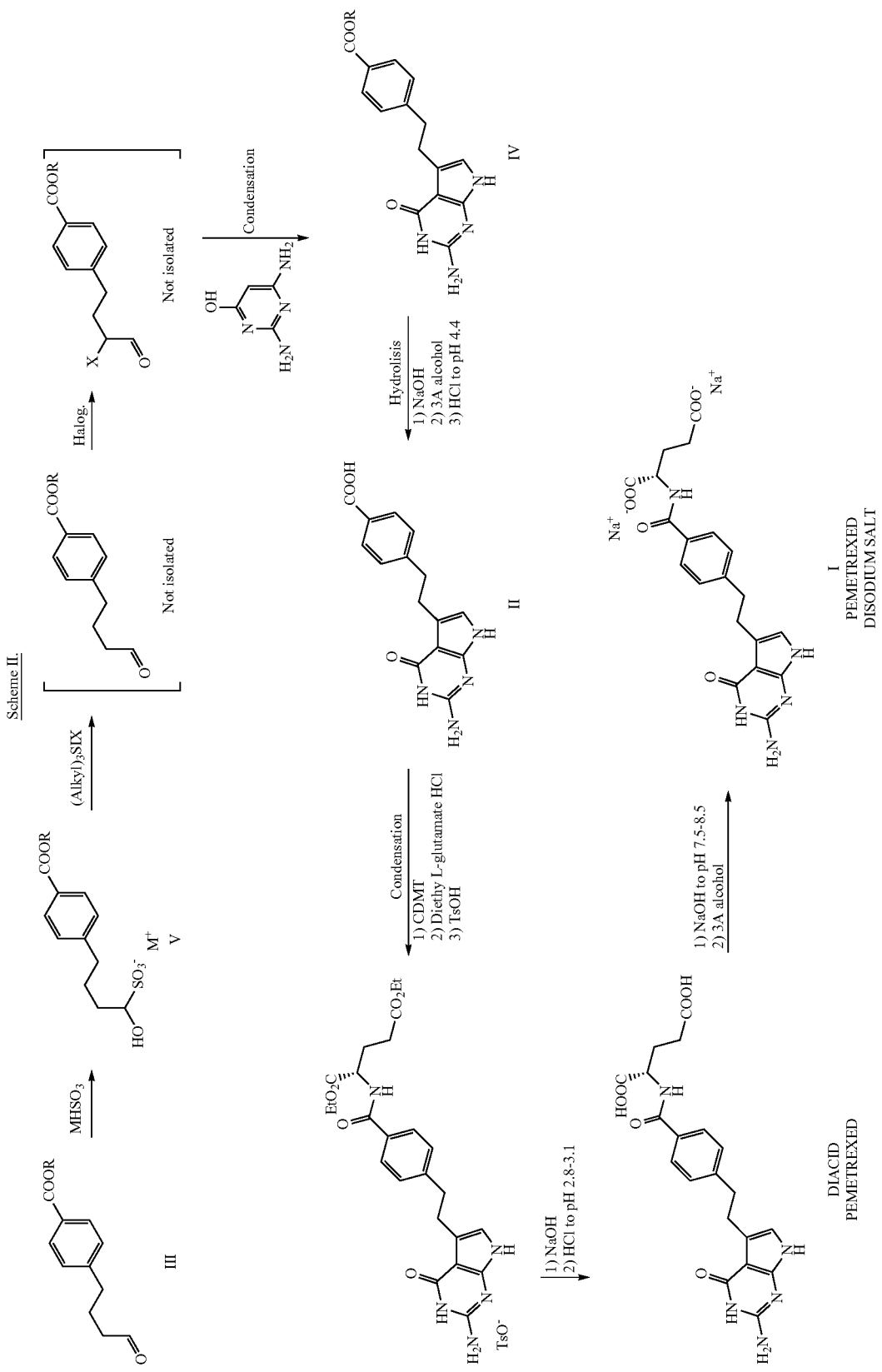

Another process is disclosed in C. J. Barnett, et al., "A Practical Synthesis of Multitargeted Antifolate LY231514," *Organic Process Research & Development*, 3 (3): 184-188 (1999) and is illustrated by the following scheme III.

followed by brominating with 3,5-di-tert-butyl-4-hydroxy benzyl acrylate ("DBBA") and HBr to obtain compound 9. Then compound 9 is transformed to compound II by the same condensation as described above.

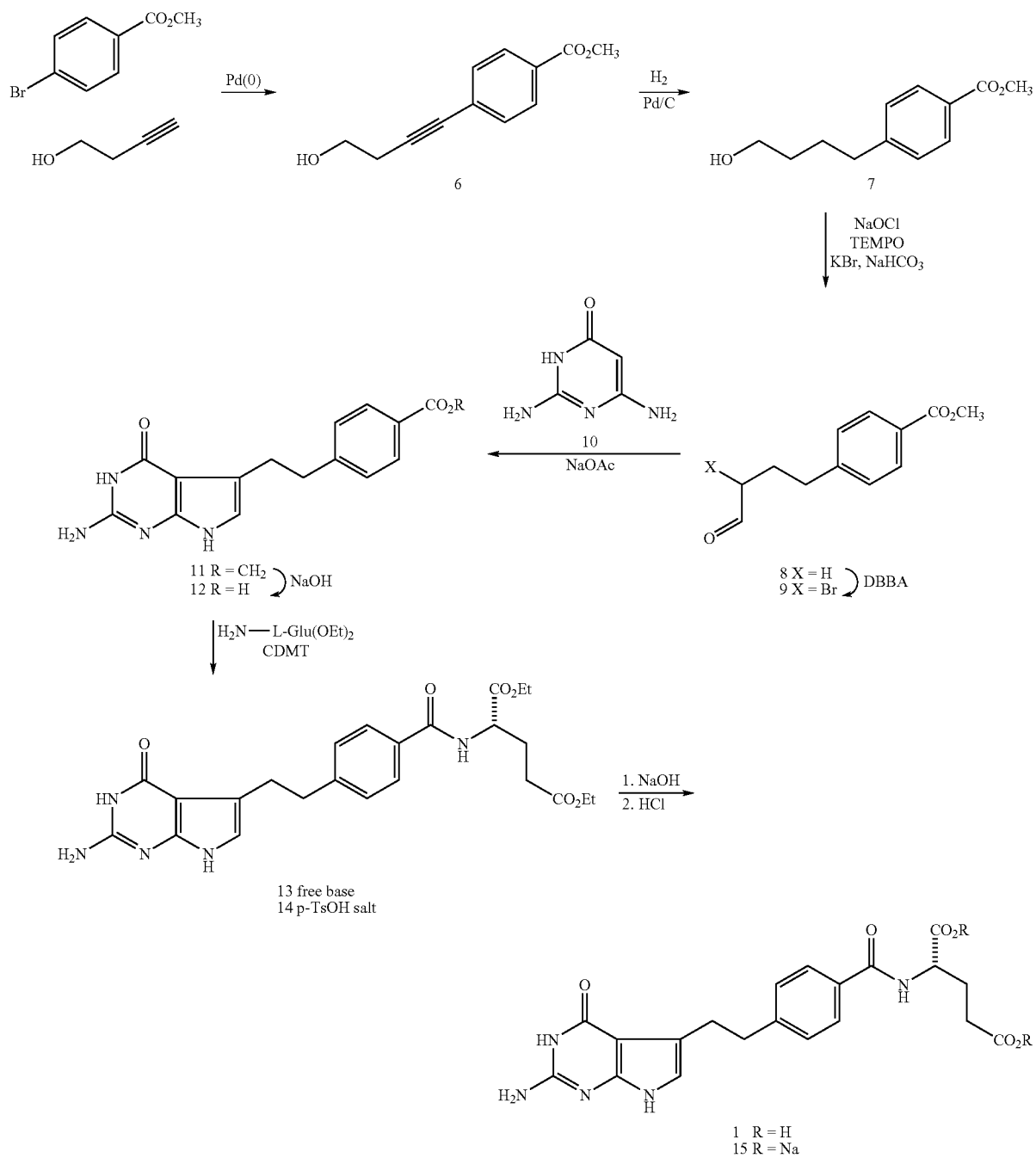

Compound 9 is obtained by coupling methyl 4-bromobenzoate and 3-butyn-1-ol in the presence of a Palladium catalyst (Heck reaction), followed by catalytically reducing the obtained alkyne with $H_2$ on Pd/C (a pyrophoric agent). The reduced alkyne of formula 7 is then oxidized with NaOCl and a 2,2,6,6-tetramethylpiperidinyloxy ("TEMPO") catalyst, Accordingly, there is a need for a concise process for preparing the pemetrexed intermediate of formula II.

SUMMARY OF THE INVENTION

In one embodiment, the invention encompasses a compound of the following formula VI

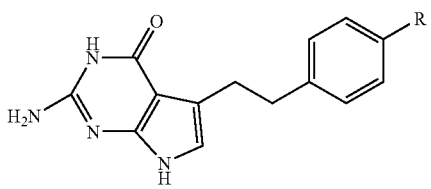

wherein R is CN, CONR'R",

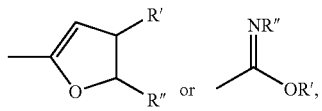

and R' and R" are independently H, alkyl or aryl.

In another embodiment, the invention encompasses a process for preparing the compound of formula VI comprising:
a) reacting a compound of the following formula VII

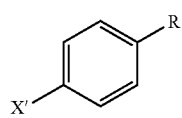

a compound of the following formula VIII,

and a catalyst suitable for Heck-coupling reactions to obtain a compound of the following formula IX;

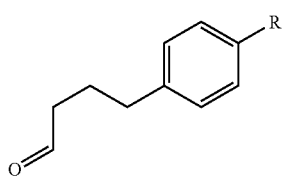

b) reacting the compound of formula IX and a halogenating agent to obtain a compound of the following formula X

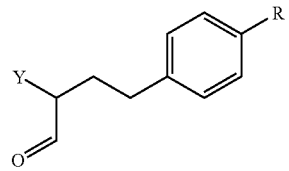

c) reacting the compound of formula X and 2,4-diamino-6-hydroxy pyrimidine to obtain the compound of formula VI; and, optionally, d) recovering the compound of formula VI, wherein X' is a leaving group; R is CN, CONR'R",

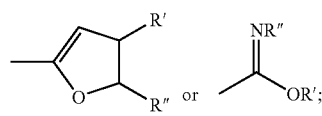

R' and R" are independently H, alkyl or aryl; X" is either O or S; and Y is a halogen leaving group.

In another embodiment, the invention encompasses a process for preparing pemetrexed or a salt thereof of the following formula, ![Pemetrexed structure with COOM1 and COOM2 groups]

comprising: a) preparing the compound of formula VI by the above-described process; and b) converting the compound of formula VI into pemetrexed or a salt thereof, wherein, M₁ and M₂ are independently either an alkali metal or H.

In another embodiment, the invention encompasses a process for preparing a compound of the following formula II ![Formula II structure with COOM group]

from the compound of formula VI comprising hydrolyzing the compound of formula VI with at least one strong base to obtain the compound of formula II, and, optionally, recovering the compound of formula II, wherein M is either an alkali metal or H.

In another embodiment, the invention encompasses a process for preparing the compound of formula II from the compound of formula VII comprising: a) reacting a compound of the following formula VII

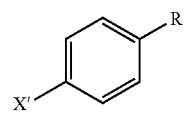

a compound of the following formula VIII,

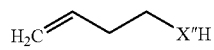

and a catalyst suitable for Heck-coupling reactions to obtain a compound of the following formula IX;

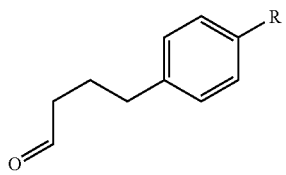

IX

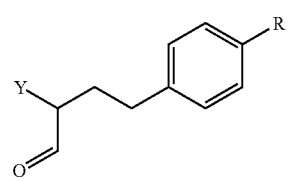

X wherein R is CN, CONR'R",

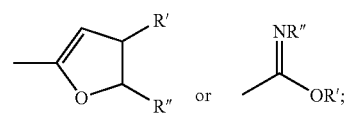

R' and R" are independently H, alkyl or aryl; and Y is a halogen leaving group.

In yet another embodiment, the invention encompasses a process for preparing the compound of formula X comprising a) reacting a compound of the following formula VII

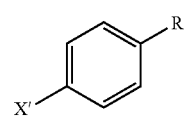

VII b) reacting the compound of formula IX and a halogenating agent to obtain a compound of the following formula X;

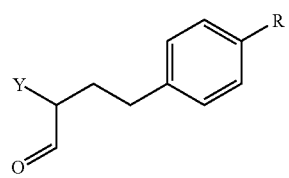

X a compound of the following formula VIII,

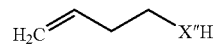

VIII and a catalyst suitable for Heck-coupling reactions to obtain a compound of the following formula IX;

c) reacting the compound of formula X and 2,4-diamino-6-hydroxy pyrimidine to obtain the compound of formula VI; d) optionally recovering the compound of formula VI, e) hydrolyzing the compound of formula VI with at least one strong base to obtain the compound of formula II, and f) optionally recovering the compound of formula II, wherein X' is a leaving group, R is CN, CONR'R",

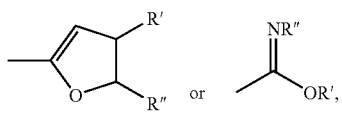

and R' and R" are independently H, alkyl or aryl, X" is either O or S, Y is a halogen leaving group.

In another embodiment, the invention encompasses a process for preparing pemetrexed or a salt thereof of the following formula,

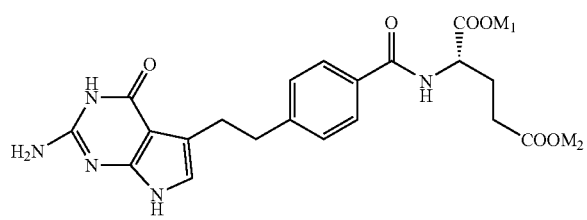

comprising: a) preparing the compound of formula II by the above-described process; and b) converting the compound of formula II into pemetrexed or a salt thereof, wherein, $M_1$ and $M_2$ are independently either an alkali metal or H.

In another embodiment, the invention encompasses a compound of the following formula X

IX

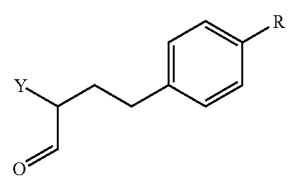

b) reacting the compound of formula IX and a halogenating agent to obtain a compound of the following formula X,

X

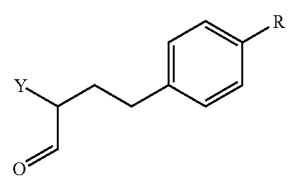

and optionally, c) recovering the compound of formula X; wherein X' is a leaving group, R is CN, CONR'R",

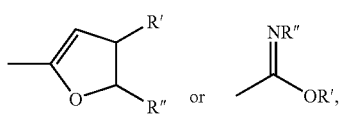

R' and R" are independently H, alkyl or aryl, X" is either O or S, and Y is a halogen leaving group.

In one embodiment, the invention encompasses a process for preparing pemetrexed or a salt thereof of the following formula,

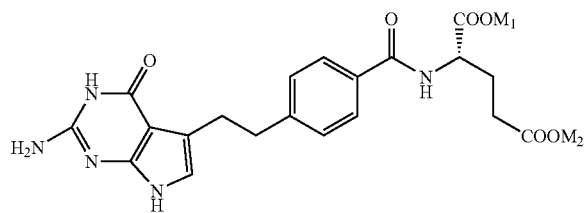

comprising: a) preparing the compound of formula X by the above-described process; and b) converting the compound of formula X into pemetrexed or a salt thereof, wherein, $M_1$ and $M_2$ are independently either an alkali metal or H.

DETAILED DESCRIPTION OF THE INVENTION

The invention provides an improved process for preparing a pemetrexed intermediate of the following formula II (wherein M is H or an alkali metal).

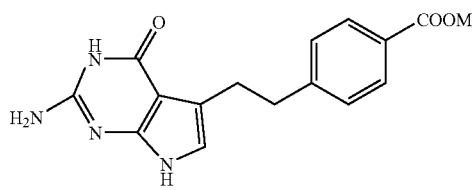

In the process of the invention, the pemetrexed intermediate of formula II may be prepared, preferably in high purity, via a straight-forward process without the need for the purification of intermediates. A highly pure intermediate of formula II may be converted to highly pure pemetrexed and salts thereof.

As used herein, unless otherwise defined, the term "pemetrexed" refers to N-[4-[2(2-amino-4,7-dihydro-4-oxo-1H-pyrrolo[2,3-d]pyrimidin-5-yl)ethyl]benzoyl]-L-glutamic acid (or "pemetrexed diacid") having the following chemical structure

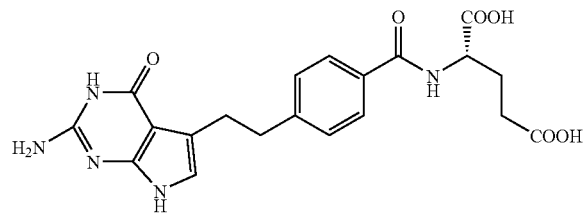

As used herein, unless otherwise defined, a pemetrexed "salt" refers to any pharmaceutically acceptable salt of pemetrexed. Preferably, the pharmaceutically acceptable salt is a metal salt, especially a di-valent metal salt, and more preferably an alkali metal salt. The metal salt can be either a mono-metal salt (i.e., only one of the carboxyl groups is coordinated to a metal ion) or a di-metal salt (i.e., both of the carboxyl groups are coordinated to a metal ion) as illustrated below.

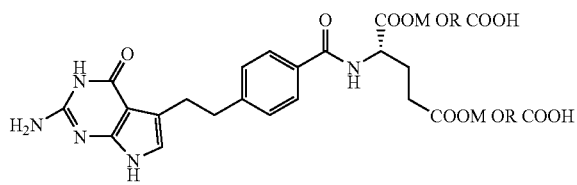

As used herein, unless otherwise defined, the term "highly pure" or "high purity" when referring to the pemetrexed intermediate of formula II means at least about 93% area by HPLC. Preferably, the pemetrexed intermediate of formula II has a purity of at least about 95% area by HPLC, more preferably at least 98% area by HPLC, especially at least 99%, and most preferably at least 99.5%, e.g., about 99.6% area by HPLC.

As used herein, unless otherwise defined, the term "highly pure" or "high purity" when referring to pemetrexed or salts thereof, means at least about 93% area by HPLC. Preferably, the pemetrexed or salt thereof has a purity of at least about 95% area by HPLC, more preferably at least 98% area by HPLC, especially at least 99%, and most preferably at least 99.5%, e.g., about 99.6% area by HPLC.

As used herein, unless otherwise defined, the term "aryl" means a compound whose molecules have the ring structure characteristic of benzene, naphthalene, phenanthrene, anthracene, etc. (i.e., either the 6-carbon ring of benzene or the condensed 6-carbon rings of the other aromatic derivatives. Preferred aryls contain 6-14, 6-10 or 6-9 carbon atoms, wherein the aryl group may include substituents, such as one or more alkyl groups (preferably $C_{1-6}$ alkyl and more preferably $C_{1-3}$ alkyl, especially methyl).

The time periods described herein are time periods suitable for laboratory-scale preparations. One of ordinary skill in the art understands that suitable time periods will vary based upon the amounts of reagents present, and can adjust the time periods accordingly.

In one embodiment, the invention encompasses a compound of the following formula X

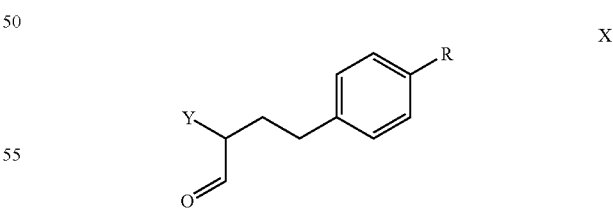

wherein R is CN, CONR'R",

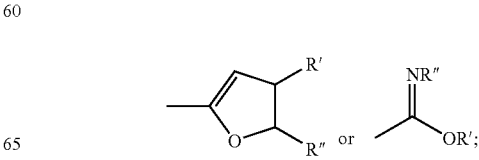

R' and R" are independently H, alkyl or aryl; and Y is a halogen leaving group.

Preferably, R is CN. Preferably, R' and R" are both hydrogen.

Preferably, the alkyl is a $C_{1-8}$ alkyl, more preferably, a $C_{1-6}$ alkyl. Preferably, the $C_{1-6}$ alkyl is $C_{1-4}$ alkyl, and more preferably methyl, ethyl, propyl, butyl, or isobutyl. Even more preferably, the $C_{1-4}$ alkyl is either methyl or ethyl, and most preferably methyl. Preferably, the aryl is $C_{6-14}$ aryl, more preferably, a $C_{6-9}$ aryl. Preferably, the $C_{6-9}$ aryl is either phenyl, or tolyl and more preferably, tolyl.

Preferably, Y is iodo, bromo, or chloro, and more preferably iodo or bromo.

In another embodiment, the invention encompasses a process for preparing the compound of formula X comprising, a) reacting a compound of the following formula VII

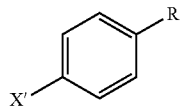

a compound of the following formula VIII,

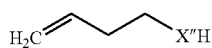

and a catalyst suitable for Heck-coupling reactions to obtain a compound of the following formula IX;

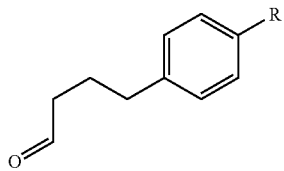

b) reacting the compound of formula IX and a halogenating agent to obtain a compound of the following formula X,

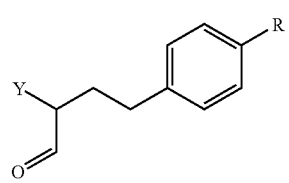

and optionally, c) recovering the compound of formula X; wherein X' is a leaving group, R is CN, CONR'R",

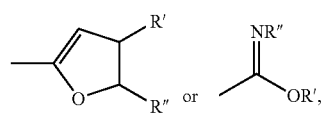

R' and R" are independently H, alkyl or aryl, X' is a leaving group, X" is either O or S, and Y is a halogen leaving group.

This process can be illustrated by the following scheme IV.

Scheme IV: Synthesis of the compound of formula X.

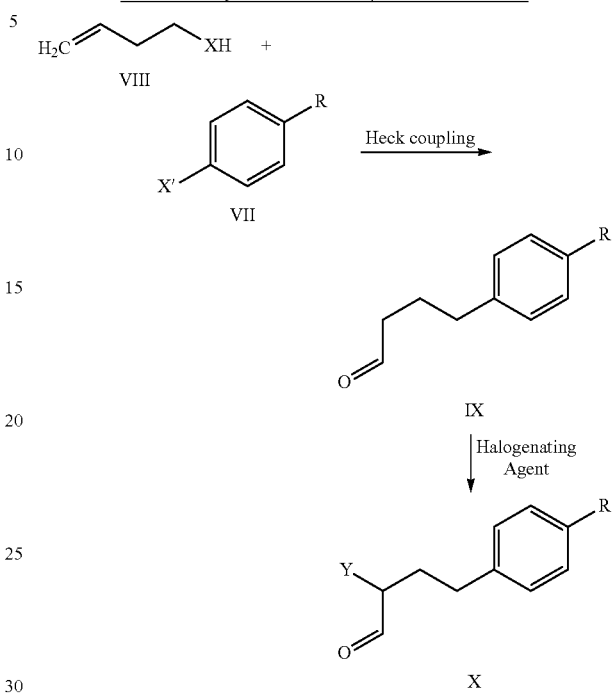

Preferably, R is CN. Preferably, R' and R" are both H. Preferably, X' is selected from the group consisting of iodo, bromo, chloro, methanesulfonyl, toluenesulfonyl and trifluoromethanesulfonyl. Preferably, X" is O. Preferably, Y is chloro, bromo or iodo, and more preferably iodo or bromo. Preferably, compound VII is 4-bromobenzonitrile. Preferably, compound VIII is 3-buten-1-ol.

Typically, the compound of formula VII is reacted with the compound of formula VIII and the catalyst in the presence of at least one polar aprotic organic solvent or at least one ionic liquid, and at least one weak base.

Preferably, the polar aprotic organic solvent is selected from the group consisting of amides, sulfoxides, pyrrolidones, ethers, halogenated hydrocarbons, and ketones. Preferably, the amide is a $C_{2-6}$ amide, such as dimethylformamide ("DMF"). Preferably, the sulfoxide is a $C_{2-4}$ sulfoxide, such as dimethylsulfoxide ("DMSO"). A preferred pyrrolidone is a $C_{4-6}$ pyrrolidone such as N-methylpyrrolidone ("NMP"). A preferred ether is a $C_{4-6}$ ether such as tetrahydrofuran ("THF"), diisopropylether ("DIPE"), or methyltertbutylether ("MTBE"). Preferably, the halogenated hydrocarbon is a $C_{1-3}$ halogenated hydrocarbon, such as 1,1-dichloroethane ("DCE"). Preferably, the ketone is a $C_{3-6}$ ketone, such as acetone, methyl isobutyl ketone ("MIBK"), or methyl ethyl ketone ("MEK").

Ionic liquids typically include salts having a relatively low melting point, such as below 150° C., more preferably below 120° C. and most preferably below 100° C., and especially below 50° C. Particularly preferred ionic liquids are those that are liquid at room temperature, wherein room temperature refers to a temperature range of about 18° C. to about 35° C., preferably about 20° C. to 25° C. Preferably, the ionic liquid may include methylimidazolium or pyridinium ions with halogen ions or tetrafluoroborate anion.

Suitable weak bases include any weak base known to one of ordinary skill in the art. Typically, the weak base has a pKa of about 7.5 to about 10.5. The weak base can be an inorganic weak base or an organic weak base. In some embodiments, the weak inorganic base is selected from the group consisting of lithium acetate, lithium bicarbonate, sodium acetate, and sodium bicarbonate, potassium bicarbonate, sodium carbonate, and potassium carbonate. In other embodiments, the weak organic base is a trialkyl amine, preferably a tri($C_{1-4}$) alkyl amine, where the alkyl groups are the same or different. Preferably, the weak organic base is selected from the group consisting of triethylamine and diisopropylethylamine.

An agent capable of increasing the polarity of a mixture can optionally be used in combination with the weak base. Examples of suitable agents include, but are not limited to, halide salts of alkali or alkaline earth metals. Preferably, the agent is lithium chloride or sodium chloride.

Suitable catalysts include any catalyst known to one of ordinary skill in the art to catalyze a Heck-coupling reaction. Preferably, the catalyst is a palladium (0 or II) catalyst, which can be also chiral. Preferably, the palladium catalyst is selected from the group consisting of palladium (II) acetate, palladium (II) propionate, palladium (II) chloride, Pd tetrakis ($PPh_3$), palladium di(dibenzylideneacetone), and palladium dichloro, 1,1'-bis(diphenylphosphino)ferrocene. Most preferably, the palladium catalyst is palladium acetate. Optionally, a mixture of catalysts may be used.

Preferably, the compound of formula VII may be reacted with the compound of formula VIII and the catalyst in the presence of a phase transfer catalyst ("PTC"). Typically, the phase transfer catalyst is selected from the group consisting of tetraalkylammonium halides, tetraarylammonium halides, and tetra(alkyl)(aryl) ammonium halides, wherein the alkyl and aryl are the same or different. Preferably the alkyl is $C_{1-6}$ alkyl. Preferably, the aryl is $C_{6-10}$ aryl. Preferably, the halide is chloride or bromide. The phase transfer catalyst is preferably selected from the group consisting of tetrabutylammonium chloride, tetrabutylammonium bromide, tetraethylammonium chloride, tetraethylammonium bromide, triethylbenzylammonium chloride, and triethylbenzylammonium bromide.

Typically, the compound of formula VII, the phase transfer catalyst, and the weak base are dissolved in the polar aprotic organic solvent. Then, the catalyst and the compound of formula VII are added to the solution to obtain a reaction mixture. The reaction mixture is then heated to obtain the compound of formula IX. Preferably, the reaction mixture is heated to a temperature of about 40° C. to about 100° C., and more preferably to a temperature of about 60° C. to about 70° C., for sufficient time to obtain the compound of formula IX. Preferably, the reaction mixture is heated with stirring. Preferably, the reaction mixture is heated for about 8 to about 20 hours, and more preferably for about 9 to about 11 hours.

The progress of the reaction to obtain the compound of formula IX may be monitored by HPLC, for example, by monitoring the amount of remaining starting material, the compound of formula VII.

The compound of formula IX may be recovered before reacting with the halogenating agent. Preferably, the compound of formula IX is recovered in the form of a solution. The recovery can be done by any method known to one of ordinary skill in the art. Preferably, the solution of the compound of formula IX is recovered in such a way to avoid or minimize its decomposition. Such methods include, but are not limited to, extraction. Preferably, a solution of the compound of formula IX is recovered by cooling the heated reaction mixture; adding a water immiscible organic solvent and water to the reaction mixture to provide a biphasic mixture having an aqueous and an organic phase; stirring the biphasic mixture; separating the phases; extracting the aqueous phase with the water immiscible organic solvent, washing the organic phase with brine, and partially removing the solvent to obtain a concentrated solution of the compound of formula IX. Preferably, the water immiscible solvent is ethyl acetate or dichloromethane. Preferably, the heated reaction mixture is cooled to a temperature of about 25° C. Preferably, the solvent is removed under vacuum at a temperature of below 40° C., more preferably at about 37° C.

The concentrated solution of the compound of formula IX can be reacted with the halogenating agent without the need to isolate the compound of formula IX from the solution.

Typically, the solution of the compound of formula IX is reacted with the halogenating agent in the presence of at least one polar aprotic organic solvent. The polar aprotic organic solvent may be the same as the one used in the coupling reaction of the compounds of formulas VII and VIII described above. Preferably, the polar aprotic organic solvent is selected from the group consisting of ethers, nitriles, amides, and sulfoxides. Preferably, the ether is a $C_{4-6}$ ether, such as THF. Preferably, the nitrile is a $C_{2-3}$ nitrile, such as acetonitrile ("ACN"). Preferably, the amide is a $C_{4-6}$ amide, such as dimethylformamide ("DMF") or dimethylacetamide ("DMA."). Preferably, the sulfoxide is a $C_{2-4}$ sulfoxide, such as DMSO. More preferably, the polar aprotic organic solvent is ACN.

Typically, the polar aprotic organic solvent is combined with the solution of the compound of formula IX to provide a second solution. Preferably, the second solution is cooled to a temperature of about 15° C. to about −15° C., and more preferably to about 5° C. to about −5° C., prior to the addition of the halogenating agent. 1) The halogenating agent is then added to the cooled second solution to obtain a mixture. Preferably, the halogenating agent is N—Br, N—Cl, or N—I succinimide; dibromantine; N—Br, N—Cl or N—I phthalimide; $Br_2$; or $Cl_2$, and more preferably $Br_2$.

The mixture may be heated for a sufficient time to obtain the compound of formula X. Preferably, the mixture is heated to about 15° C. to about 35° C., and more preferably to about 20° C. to about 30° C. to obtain the compound of formula X. Preferably, the mixture is maintained for about 1 hour to about 4 hours, and more preferably, for about 1.5 hours to about 2.5 hours.

The compound of formula X may be recovered from the mixture. Preferably, the compound of formula X is recovered in the form of a solution. The recovery can be done by any method known to one of ordinary skill in the art. Preferably, the solution of the compound of formula X is recovered in such a way to avoid or minimize its decomposition. Such methods include, but are not limited to, extraction. Preferably, the recovery is done by adding to the maintained mixture water and a sulfur reducing agent; adding a water immiscible organic solvent and water to form a biphasic mixture having an aqueous and an organic phase, and separating and concentrating the organic phase. Preferably, the sulfur reducing agent is selected from the group consisting of sodium bisulfite, sodium thiosulfate, and potassium thiosulfate and more preferably, sodium bisulfate. Preferably, the water immiscible organic solvent is toluene, ethyl acetate, methylisobutyl ketone, methyl tert-butyl ether, or DCM. Preferably, adding water and a sulfur reducing agent provides a new mixture. Preferably, the new mixture is stirred for about 1 hour. Preferably, the organic phase is concentrated under vacuum at a temperature of about 37° C.

In another embodiment, the compound of formula X thus obtained can be converted to pemetrexed or a salt thereof of the following formula,

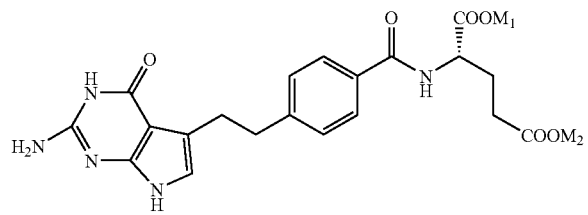

wherein $M_1$ and $M_2$ are independently either an alkali metal or H.

According to the process of the invention, the conversion of compound X to pemetrexed or a salt thereof is done through the compound of formula II, which is prepared from the compound of formula VI. This conversion is illustrated by the following scheme V:

Scheme V: Preparation of the compound of formula II from the compound of formula X via the compound of formula VI

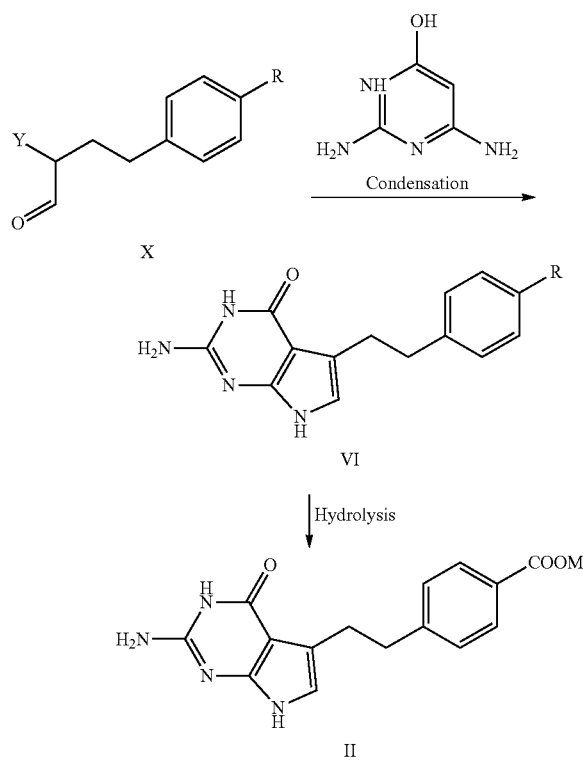

wherein R and Y are described before, and M is either an alkali metal or H.

The solution of the compound of formula X obtained by the above-described process can be reacted with the 2,4-diamino-6-hydroxy pyrimidine to give the compound of formula VI without the need to isolate the compound of formula X from the solution.

In one embodiment, the invention encompasses the compound of formula VI;

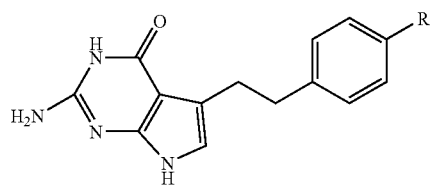

wherein R is CN, CONR'R", and R' and R" are

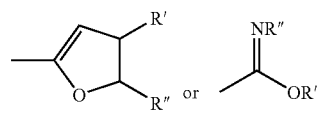

independently H, alkyl or aryl.

Preferably, R is CN. Preferably, R' and R" are both hydrogen.

Preferably, the alkyl is a $C_{1-8}$ alkyl, more preferably, a $C_{1-6}$ alkyl. Preferably, the $C_{1-6}$ alkyl is $C_{1-4}$ alkyl, and more preferably methyl, ethyl, propyl, butyl, or isobutyl. Even more preferably, the $C_{1-4}$ alkyl is either methyl or ethyl, and most preferably methyl. Preferably, the aryl is $C_{6-14}$ aryl, more preferably, a $C_{6-9}$ aryl. Preferably, the $C_{6-9}$ aryl is either phenyl, or tolyl and more preferably, tolyl.

When R is CN, said compound of formula VI corresponds to 4-[2-(2-amino-4,7-dihydro-4-oxo-3H-pyrrolo[2,3-d]pyrimidin-5-yl)ethyl]benzonitrile of the following formula.

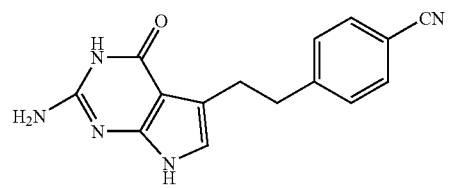

The 4-[2-(2-amino-4,7-dihydro-4-oxo-3H-pyrrolo[2,3-d]pyrimidin-5-yl)ethyl]benzonitrile can be characterized by an $^1$HNMR (DMSO-$d_6$) spectrum with peaks at: 2.84, 3.02, 6.00, 6.30, 7.39, 8.3, 7.71, 10.15, and 10.62 ppm. The above 4-[2-(2-amino-4,7-dihydro-4-oxo-3H-pyrrolo[2,3-d]pyrimidin-5-yl)ethyl]benzonitrile can be also characterized by an MS (ES) having an [(M+H)$^+$] peak at m/z 280.

As mentioned before, the compound of formula VI is used to prepare pemetrexed or salt thereof. The use of the pemetrexed intermediate of formula VI, where R is CN, i.e., 4-[2-(2-amino-4,7-dihydro-4-oxo-3H-pyrrolo[2,3-d]pyrimidin-5-yl)ethyl]benzonitrile, provides an advantage over use of the pemetrexed intermediate of the following formula IV (disclosed in the '262 patent)

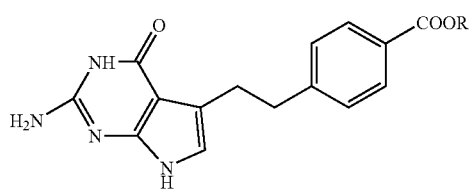

because cyano derivatives are typically more crystalline, and, thus, easier to crystallize and purify than ester derivatives. Accordingly, it is believed that use of the cyano intermediate of the invention may allow one to achieve pemetrexed in higher purity than can be achieved via the ester intermediate of the '262 patent.

In one embodiment, the present invention encompasses a process for preparing the compound of formula VI. The process comprises reacting the compound of formula X and 2,4-diamino-6-hydroxy pyrimidine of the formula

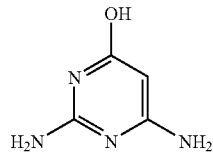

to obtain the compound of formula VI; and optionally recovering the compound of formula VI.

The compound of formula X can be used in the form of the solution obtained by the above-described process, without further isolation. Typically, the solution of the compound of formula X is reacted with the 2,4-diamino-6-hydroxy pyrimidine in the presence of water and at least one weak base. The weak base may be the same as the one used in the coupling reaction of the compounds of formulas VII and VIII described above. The weak base may be an inorganic weak base or an organic weak base. Preferably, the weak inorganic base is selected from the group consisting of lithium acetate, sodium acetate, and sodium bicarbonate, and more preferably sodium acetate. Preferably, the weak organic base is selected from the group consisting of triethylamine and diisopropylethylamine. Most preferably, the weak base is lithium acetate.

Typically, the 2,4-diamino-6-hydroxy pyrimidine is added to a mixture of the solution the compound of formula X, the weak base and water to provide a reaction mixture. The reaction mixture may then be heated to obtain the compound of formula VI. Preferably, the reaction mixture is heated to a temperature of about 20° C. to about 40° C., and more preferably to about 35° C. to about 40° C. for a sufficient time to obtain the compound of formula VI. Preferably, the reaction mixture is heated for about 1 hour to about 4 hours, and more preferably for about 1.5 hours to about 2.5 hours.

The compound of formula VI may be recovered from the reaction mixture by any method known to one of ordinary skill in the art. Such methods include, but are not limited to, precipitating the compound of formula VI from the reaction mixture and filtering the precipitate. Preferably, the compound of formula VI is recovered by cooling the heated reaction mixture to provide a suspension having a precipitate of the compound of formula VI; maintaining the suspension; filtering the suspension to isolate the precipitate; washing the precipitate; and drying the precipitate. Preferably, the heated reaction mixture is cooled to a temperature of about 24° C. Preferably, the suspension is maintained for about 42 hours while being stirred.

The compound of formula VI thus obtained has a chemical purity of at least about 93% area by HPLC, preferably at least about 95.5% area by HPLC, and more preferably at least about 98% area by HPLC.

In another embodiment, the compound of formula VI thus obtained may be converted into pemetrexed or a salt thereof of the following formula,

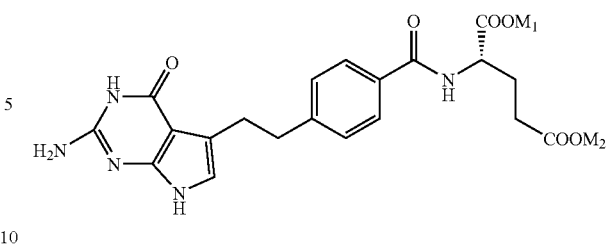

Wherein $M_1$ and $M_2$ are independently either an alkali metal or H.

According to the process of the invention, this conversion is done through the compound of formula II.

In another embodiment, the invention encompasses a process for converting the compound of formula VI to the compound of formula II. The process comprises hydrolyzing the compound of formula VI with at least one strong base to obtain the compound of formula II, and recovering the compound of formula II.

Typically, the hydrolysis is done in the presence of a solvent. The solvent can be water or a mixture of water and at least one polar solvent. Examples of suitable polar solvents include, but are not limited to, amides, sulfoxides, and alcohols. Preferably, the amide is DMF. Preferably, the sulfoxide is DMSO. A preferred alcohol is a $C_{1-4}$ alcohol. Preferably, the $C_{1-4}$ alcohol is methanol, ethanol, propanol, isopropanol, butanol or iso-butanol.

Suitable strong bases include any strong base known to one of ordinary skill in the art. Typically, the strong base is one that completely dissociates in water. Preferably, the strong base is an inorganic base. Preferably, the inorganic base is an alkaline base. Preferably, the alkaline base is an alkaline hydroxide. Preferably, the alkaline hydroxide is selected from the group consisting of sodium hydroxide, lithium hydroxide, and potassium hydroxide.

Typically, the compound of formula VI, the strong base, and the solvent are combined to obtain a suspension. The suspension is then heated to obtain a solution of the compound of formula II. Preferably, the suspension is heated to a temperature of about 70° C. to about 100° C., and more preferably, about 90° C. to about 100° C. for a sufficient time to obtain the compound of formula II. Preferably, the suspension is heated for about 2 hours to about 4 hours, more preferably, for about 3 hours to about 4 hours.

The compound of formula II may be recovered by a process comprising: cooling the solution; adjusting the pH of to the solution to about 6 to about 10 to obtain a suspension, and recovering the compound of formula II from the suspension (e.g., by filtering the suspension to obtain the compound of formula II); and, optionally, drying the compound of formula II. Preferably, the solution is cooled to a temperature of about 30° C. to about 5° C., and more preferably to about 25° C. to about 15° C. Preferably, cooling is conducted over a period of about 1 hour to about 2 hours, and more preferably for about 1.5 hours to about 2 hours. Preferably, the pH of the solution is adjusted to about 6 to about 10, more preferably about 7.5 to about 9.5, and even more preferably about 8.5 to about 9.5, by the addition of a diluted acid to the cooled solution. Preferably, the acid is selected from the group consisting of HCl, $H_2SO_4$, $HNO_3$, HBr, trifluoroacetic acid, trichloroacetic acid, and alkyl and aryl sulfonic acids. More preferably, the acid is HCl. Preferably, the diluted acid has a concentration of about 0.1M to about 2M, and more preferably about 0.1M to about 1M. Preferably, the compound of formula II is dried under vacuum with heating. For example, the compound of formula II may be dried at a temperature of about 60° C. at a pressure of about 18 mbar for about 16 hours.

The compound of formula II thus obtained preferably has a chemical purity of at least about 93% area by HPLC, preferably at least about 95% area by HPLC, more preferably at least about 98% area by HPLC, and most preferably about 99.6% area by HPLC.

Optionally, the compound of formula II may be further purified. The compound of formula II is purified by a process comprising providing a solution of the compound of formula II having a pH of about 10 to about 14; decreasing the pH to about 6 to about 10 to precipitate the purified compound of formula II; and recovering the purified compound of formula II.

Typically, the solution of the compound of formula II having a pH of about 10 to about 14 is provided by combining the compound of formula II with a strong base. Preferably, the pH is about 11 to about 13. Preferably, the strong base is an alkaline hydroxide, and more preferably sodium hydroxide. Preferably, an aqueous solution of the strong base is combined with the compound of formula II. The solution of the compound of formula II having a pH of about 10 to about 14 may also contain a water miscible organic solvent, such as ethanol, methanol or acetone.

Preferably, the pH of the solution is decreased to about 6 to about 10 by combining the solution with an acid. Preferably, the pH of the solution is decreased to about 7.5 to about 9.5, and more preferably about 8.5 to about 9.5. Preferably, the acid is selected from the group consisting of HCl, $H_2SO_4$, $HNO_3$, HBr, trifluoroacetic acid, trichloroacetic acid, and alkyl and aryl sulfonic acids. Preferably, a diluted acid is combined with the solution. Preferably, the diluted acid has a concentration of about 0.1M to about 2M, and more preferably about 0.1M to about 1M.

Preferably, combining the acid with the solution provides a suspension. Preferably, the suspension is maintained, while being stirred, for about 1 hour to about 3 hours. The purified compound of formula II may be recovered from the suspension by filtering, washing the solid with water or, optionally, with an aqueous solution having a pH of about 9, and drying.

In yet another embodiment, the compound of formula II obtained by the above-described process may be converted into pemetrexed or a salt thereof of the following formula

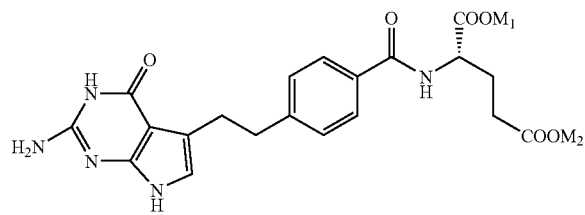

where $M_1$ and $M_2$ are described before. The conversion can be done, for example, by the process disclosed in U.S. Pat. No. 6,262,262, hereby incorporated by reference, The compound of formula II may be used with or without purification to prepare pemetrexed or a salt thereof.

Having described the invention with reference to certain preferred embodiments, other embodiments will become apparent to one of ordinary skill in the art from consideration of the specification. The invention is further defined by reference to the following examples. It will be apparent to those of ordinary skill in the art that many modifications, both to materials and methods, may be practiced without departing from the scope of the invention.

EXAMPLES

Example 1

Preparation of 4-(4-benzonitrile)-butanal (compound IX)

4-bromobenzonitrile (20 g, 109.87 mmol), lithium acetate (12.33 g, 120.86 mmol), lithium chloride (13.97 g, 329.62 mmol), and tetrabutylammonium chloride (14.35 g, 51.64 mmol) were dissolved in 274 ml of dimethylformamide. The resulting solution was degassed with a subsurface nitrogen purge. 3-Buten-1-ol (9.51 g, 11.30 mL, 131.85 mmol) and palladium acetate (672 mg, 2.75 mmol) were added to the solution and the reaction mixture was heated to 65° C., while stirring under nitrogen atmosphere, for approximately 17 h. The progress of the reaction was monitored by HPLC by the amount of starting 4-bromobenzonitrile remaining. The reaction was deemed to be complete when there was <0.4% 4-bromobenzonitrile remaining, as determined by HPLC. After the reaction was complete, the reaction mixture was allowed to cool to 25° C. spontaneously and water (200 mL) and ethyl acetate (200 mL) were added. The reaction mixture was then stirred for 10 more minutes and subsequently the layers were allowed to separate. The organic layer was retained and the aqueous layer was extracted two times with ethyl acetate (200 mL). All the organic phases were combined, washed with brine (100 mL) and dried with sodium sulfate. The resulting solution of the title compound was concentrated at 37° C. until a volume of 70 mL was obtained and was stored under ambient conditions.

Example 2

Preparation of 1-Hydroxy-2-bromo-4-(4-benzonitrile) butanal (compound X)

The ethyl acetate solution of 4-(4-benzonitrile)-butanal prepared in example 1 was evaporated three times after consecutive additions of acetonitrile in portions (3×70 mL), until substitution of ethyl acetate with acetonitrile. Nitrogen was bubbled through the resulting solution for 10 minutes, the mixture was cooled to 5° C. with a cooling bath, and bromine (17.6 g, 5.6 mL, 109.87 mmol) was added to obtain an orange solution. The solution was then removed from the cooling bath and was stirred for additional 2 hours. Water (100 mL) and sodium bisulfite (1.1 g, 10.90 mmol) were added in order to quench the remaining bromine and the resulting mixture was stirred for 1 hour. The mixture was then partitioned between methylene chloride (100 mL) and an additional quantity of water (50 mL). The organic phase was separated and concentrated at 37° C. to a volume of 210 mL. The resulting solution of the title compound 1-hydroxy-2-bromo-4-4(4-cyanophenyl)butanal was not isolated or further purified before subsequent reaction.

Example 3

Preparation of 4-[2-(2-amino-4,7-dihydro-4-oxo-3H-pyrrolo[2,3-d]pyrimidin-5-yl)ethyl]benzonitrile (compound VI)

To 70 mL of the methylene chloride solution from example 2, containing 1-hydroxy-2-bromo-4-4(4-cyanophenyl)butanal, were added water (60 mL) and sodium acetate (4.20 g, 51.19 mmol). Nitrogen was bubbled through the mixture for 10 minutes and 2,4-diamino-6-hydroxy pyrimidine (3.20 g, 25.37 mmol) was added. The mixture was heated at 40° C., under nitrogen atmosphere, for 2 hours and then was allowed to cool to 24° C. spontaneously. The suspension was stirred at 24° C. for 42 hours, left standing for 2 hours without stirring and filtered. The collected solid was washed with a 1:1 mixture of acetonitrile and water (70 mL). The filter cake was dried under vacuum for 2 hours at 40° C. to yield 1.0 g of the title compound as a white powder (HPLC purity 95.8%).

Example 4

Preparation of a mixture of 4-[2-(2-amino-4,7-dihydro-4-oxo-3H-pyrrolo[2,3-d]pyrimidine-5-yl)ethyl] benzoic acid and its sodium salt (compound II)

Step a. Preparation of 4-[2-(2-amino-4,7-dihydro-4-oxo-3H-pyrrolo[2,3-d]pyrimidine-5-yl)ethyl]benzoic acid, sodium salt A flask was charged with 4-[2-(2-amino-4,7-dihydro-4-oxo-3H-pyrrolo[2,3-d]pyrimidine-5-yl)ethyl]benzonitrile (4.1 g) and a 2M sodium hydroxide aqueous solution (40 mL). The suspension was stirred at 90° C. for 3 hours, during which a clear solution was obtained. The solution was then cooled to 24° C. over 1.5 hours, and the pH was adjusted to 9 by the addition of diluted hydrochloric acid. The resulting suspension was stirred for 1 hour, filtered, and the solid was dried in the oven under vacuum, affording the product (3.8 g) (HPLC purity 99.6%).

Step b. Conversion of 4-[2-(2-amino-4,7-dihydro-4-oxo-3H-pyrrolo[2,3-d]pyrimidine-5-yl)ethyl]benzoic acid, sodium salt to its free acid The mixture of step a is suspended in water (6 volumes). The pH is then corrected to about 12 with a 2M solution of sodium hydroxide in water and the mixture is stirred until complete dissolution. The pH is then corrected to about 4.4 with 6N hydrochloric acid in water to obtain a suspension. Then the suspension is stirred for about 2 hours, and the 4-[2-(2-amino-4,7-dihydro-4-oxo-3H-pyrrolo[2,3-d]pyrimidine-5-yl)ethyl]benzoic acid is filtered and dried in the oven under vacuum. The 4-[2-(2-amino-4,7-dihydro-4-oxo-3H-pyrrolo[2,3-d]pyrimidine-5-yl)ethyl]benzoic acid thus prepared has a purity of about 99.6% by HPLC.

Example 5

Purification of 4-[2-(2-amino-4,7-dihydro-4-oxo-3H-pyrrolo[2,3-d]pyrimidine-5-yl)ethyl]benzoic acid (compound II)

A flask was charged with 4-[2-(2-amino-4,7-dihydro-4-oxo-3H-pyrrolo[2,3-d]pyrimidine-5-yl)ethyl]benzoic acid (5.0 g; 93.85% purity HPLC) and water (30 ml), the pH was corrected to about 13 with a 2M sodium hydroxide solution in water, and complete dissolution was observed. The pH was then corrected to about 9 with a 1M hydrochloric acid solution in water, and abundant solid formation was observed. The resulting suspension was stirred at about 25° C. for 1 hour, the solid was collected by filtration and dried in an oven under vacuum to afford 4-[2-(2-amino-4,7-dihydro-4-oxo-3H-pyrrolo[2,3-d]pyrimidine-5-yl)ethyl]benzoic acid sodium salt as a white solid in 99.6% purity (HPLC).

$^1$H NMR (DMSO-d$_6$) δ2.84 (m, 2H), 3.02 (m, 2H), 6.00 (bs, 2H), 6.30 (bs, 1H), 7.39 (d, J=8.3 Hz, 2H), 7.71 (d, J=8.2 Hz, 2H), 10.15 (bs, 1H), 10.62 (bs, 1H); MS (ES) m/z 280 [(M+H)$^+$].

The 4-[2-(2-amino-4,7-dihydro-4-oxo-3H-pyrrolo[2,3-d]pyrimidine-5-yl)ethyl]benzoic acid sodium salt may be converted to the title compound by the procedure set forth in Example 4b above.

Example 6

Preparation of N-(4-[2-(2-amino-4,7-Dihydro-4-Oxo-1H-Pyrrolo[2,3-d]pyrimidin-5-yl)ethyl]benzoyl)-L-Glutamic Acid Diethyl Ester p-Toluenesulfonic Acid Salt (Based on U.S. Pat. No. 6,262,262)

A flask is charged with 1.93 g of 4-[2-(2-amino-4,7-dihydro-4-oxo-1H-pyrrolo[2,3-d]pyrimidin-5-yl)ethyl]benzoic acid or with the mixture obtained in example 4, and 13.5 mL of dimethylformamide. The slurry is stirred 20 minutes and 1.94 g N-methylmorpholine is added. The mixture is cooled to 5° C. and 1.46 g chlorodimethoxytriazine is added all at once. The mixture is stirred for 1 h and then 1.99 g L-glutamic acid diethyl ester hydrochloride is added. The reaction is allowed to warm to ambient temperature. The end of the reaction is monitored by HPLC after about 1 h. At that point 36 mL of water and 36 mL of dichloromethane are added to the reaction mixture which is stirred for 15 minutes and the layers are allowed to separate. The organic phase is collected and concentrated until 13 g and then replaced by 60 mL of absolute ethanol. The solution is heated at 75° C. and 3.16 g p-toluenesulfonic acid dissolved in 55 mL of ethanol absolute is added drop wise. The resulting slurry is refluxed for an hour, then cooled to ambient temperature and filtered. The wet cake is dried, washed with 25 mL ethanol, and is dried in the oven at 40° C., under vacuum overnight, to yield 3.66 g of the title compound.

Example 7

Preparation of N-(4-[2-(2-amino-4,7-Dihydro-4-Oxo-1H-Pyrrolo[2,3-d]pyrimidin-5-yl)ethyl]benzoyl)-L-Glutamic Acid (Based on U.S. Pat. No. 6,262,262)

N-(4-[2-(2-amino-4,7-dihydro-4-oxo-1H-pyrrolo[2,3-d]pyrimidin-5-yl)ethyl]benzoyl)-L-glutamic acid diethyl ester p-toluenesulfonic acid salt (1.0 g) is dissolved in 6.7 mL aqueous sodium hydroxide and stirred until complete solution is obtained. 6 mL of water is added and the pH is adjusted to 3.0-3.5 by the addition of diluted hydrochloride acid. The resulting slurry is heated at 70° C. for an hour and then filtered to yield the title compound in 99.6% purity (HPLC).

Example 8

Preparation of N-(4-[2-(2-amino-4,7-Dihydro-4-Oxo-1H-Pyrrolo[2,3-d]pyrimidin-5-yl)ethyl]benzoyl)-L-Glutamic Acid Disodium Salt according to U.S. Pat. No. 6,262,262

N-[4-[2-(2-Amino-4,7-dihydro-4-oxo-1H-pyrrolo[2,3-d]pyrimidin-5-yl)ethyl]benzoyl]-L-glutamic acid from example 7 is dissolved in water (3.8 mL) and sodium hydroxide 1N (2.2 mL). The pH of the mixture is adjusted to 7.5-8.5, by the addition of hydrochloride acid 1N. The solution is heated at 70° C. and ethanol absolute (40 mL) is added to the mixture. The solution is allowed to cool down slowly to room temperature. The slurry is filtered and washed with a mixture of ethanol absolute and water (4:1). The resulting white solid is dried in the oven at 50° C. under vacuum over 18 h.

What is claimed is:

1. A compound of the following formula VI

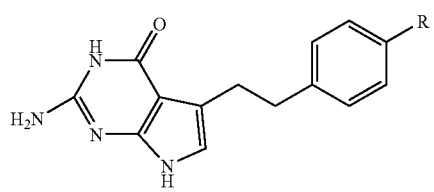

wherein R is CN,

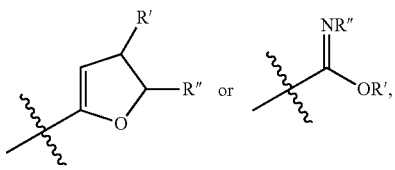

and R' and R" are independently H, $C_{1-8}$ alkyl or $C_{6-14}$ aryl, or R is $CONR^A R^B$ and $R^A$ and $R^B$ are independently H or $C_{6-14}$ aryl.

2. The compound of claim 1, wherein R is CN.

3. The compound of claim 1, wherein R' and R" are both H.

4. The compound of claim 2, characterized by an $^1$H NMR (DMSO-$d_6$) spectrum with peaks at about 2.84, 3.02, 6.00, 6.30, 7.39, 8.3, 7.71, 10.15, and 10.62 ppm.

5. The compound of claim 2, characterized by an MS (ES) having an $[(M+H)^+]$ peak at m/z 280.

6. A process for preparing a compound of the following formula VI

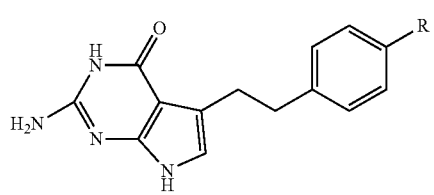

comprising reacting a compound of the following formula X

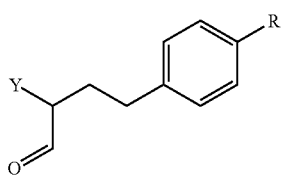

and 2,4-diamino-6-hydroxy pyrimidine to obtain the compound of formula VI,
wherein R is CN, $CONR^A R^B$

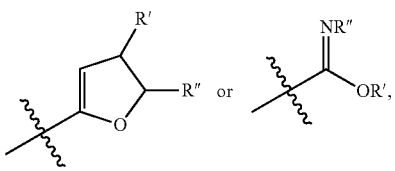

R', R", $R^A$ and $R^B$ independently H, and Y is a halogen leaving group.

7. The process of claim 6, wherein R is CN.

8. The process of claim 6, wherein Y is iodo, bromo, or chloro.

9. The process of claim 6, wherein the compound of formula X is reacted with the 2,4-diamino-6-hydroxy pyrimidine in the presence of water and at least one weak base.

10. The process of claim 9, wherein the weak base is an inorganic base.

11. The process of claim 10, wherein the inorganic base is selected from the group consisting of sodium acetate, sodium bicarbonate, potassium bicarbonate, sodium carbonate, potassium carbonate, and lithium acetate.

12. The process of claim 9, wherein the weak base is an organic base.

13. The process of claim 12, wherein the organic base is selected from the group consisting of triethylamine and diisopropylethylamine.

14. The process of claim 9, wherein the weak base is lithium acetate.

15. The process of claim 9, wherein the compound of formula X, the 2,4-diamino-6-hydroxy pyrimidine, the base and the water are heated to obtain the compound of formula VI.

16. The process of claim 15, wherein the compound of formula X, the 2,4-diamino-6-hydroxy pyrimidine, the base and the water are heated to a temperature of about 20° C. to about 40° C.

17. The process of claim 6, further comprising recovering the compound of formula VI.

* * * * *